(12) United States Patent
Bakircioğlu et al.

(10) Patent No.: US 6,733,454 B1
(45) Date of Patent: May 11, 2004

(54) AUTOMATIC OPTIMIZATION METHODS AND SYSTEMS FOR DOPPLER ULTRASOUND IMAGING

(75) Inventors: Müge M. Bakircioğlu, Sunnyvale, CA (US); Bhaskar Ramamurthy, San Jose, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 10/374,258

(22) Filed: Feb. 26, 2003

(51) Int. Cl.[7] .................................................. A61B 8/06
(52) U.S. Cl. ...................................................... 600/453
(58) Field of Search ................................ 600/437–472; 73/595–640; 367/7, 11, 130, 138; 342/88, 162; 382/128; 375/200–342; 607/9, 17, 16, 27

(56) References Cited

U.S. PATENT DOCUMENTS

| | | | |
|---|---|---|---|
| 3,858,208 A | * 12/1974 | Parke et al. | ............ 342/88 |
| 5,634,465 A | 6/1997 | Schmiesing et al. | |
| 5,690,116 A | * 11/1997 | Goujon | ........ 600/454 |
| 5,868,676 A | 2/1999 | McCabe et al. | |
| 6,142,943 A | 11/2000 | Mo et al. | |
| 6,398,733 B1 | 6/2002 | Simopoulos et al. | |
| 6,447,455 B2 | 9/2002 | Bang et al. | |
| 2002/0116141 A1 | 8/2002 | Mo et al. | |

* cited by examiner

Primary Examiner—Ali M Imam (57) ABSTRACT

Methods and systems are provided for automatic optimization of spectral Doppler ultrasound imaging. One or more of the velocity scale (e.g., pulse repetition frequency), gain, baseline, dynamic range or other imaging parameters are optimized based on one or both of: (1) determining the optimum parameter based on data acquired at a standard or predetermined setting of the parameters and (2) identifying an artifact in the Doppler ultrasound data and discarding or minimizing the influence of the artifact on any determination of imaging parameter settings. One embodiment used for cardiac Doppler imaging identifies artifact signals using the maximum or minimum traces. For example, the velocity scale or pulse repetition frequency is set based on the maximum or minimum velocity value over one or more heartbeats identified from a maximum and minimum trace of the signal envelope or Doppler spectrum. Since flows in cardiology may contain high energy, high velocity, short duration signals caused by valve clicks, these artifacts are identified and discarded in determining the maximum and minimum values.

28 Claims, 4 Drawing Sheets

AUTOMATIC OPTIMIZATION METHODS AND SYSTEMS FOR DOPPLER ULTRASOUND IMAGING

BACKGROUND

The present invention relates Doppler processing. In particular, methods and systems for automatically adjusting imaging parameters for either of radiology or cardiology Doppler imaging is provided.

For spectral Doppler imaging, a pulse or continuous wave is transmitted to a particular location in a patient. The signals received are processed using a fast Fourier transform or other frequency analysis. The resulting Doppler spectrogram shows the range of velocities modulated by an associated energy or spectral power as a function of time for the gate position. The data for each spectral line or time comprises multiple different frequency or velocity intervals where each of the frequency intervals is modulated by the spectral power for the interval, representing an instantaneous measurement of blood flow at the gate position.

Various system settings or imaging parameters affect the display of the Doppler spectrum. The pulse repetition frequency, the baseline level, the gain and the dynamic range applied by the system alter the display of the Doppler spectrum. For example, the pulse repetition frequency or velocity scale may be set to avoid aliasing while maximizing the information content or number of velocity intervals used in the displayed spectrum. As another example, the gain and/or dynamic range may be set to minimize information loss due to saturation or compression to a few values. As yet another example, the baseline may be set such that the positive or negative information are displayed with a relative amount of content, minimizing the velocity scale.

Any of the various system settings are typically controlled by the user. Some systems may automatically adjust the scale, baseline, or other parameters. Data is acquired at the user's initial or later settings, adversely affecting the performance of the automatic optimization. In one such system, a maximum and minimum trace on the envelope of the Doppler spectrum is used to determine a new pulse repetition frequency. However, artifacts in the maximum or minimum trace may adversely alter the determined pulse repetition frequency, resulting in excess unused capability of imaging the Doppler spectrum.

BRIEF SUMMARY

The present invention is defined by the following claims, and nothing in this section should be taken as a limitation on those claims. By way of introduction, the preferred embodiments described below include methods and systems for automatic optimization in Doppler ultrasound imaging. One or more of the velocity scale (e.g., pulse repetition frequency), gain, baseline, dynamic range or other imaging parameters are optimized based on one or both of: (1) determining the optimum parameter based on signal acquired at a standard or predetermined setting of the parameters and (2) identifying an artifact in the Doppler ultrasound data and discarding or minimizing the influence of the artifact on any determination of imaging parameter settings.

One embodiment used for cardiac Doppler imaging identifies artifact signals using the maximum or minimum velocity traces. For example, the velocity scale or pulse repetition frequency is set based on the maximum or minimum velocity value over one or more heartbeats identified from a maximum and minimum trace of the signal envelope or Doppler spectrum. Since flows in cardiology may contain high energy, high velocity, short duration signals caused by valve clicks, these artifacts are identified and discarded in determining the maximum and minimum velocity values.

In a first aspect, a method for automatic optimization in Doppler ultrasound imaging is provided. At least one signal or a plurality of signals from a gate position in a patient are identified. The identified signal is discarded from the plurality of signals. At least one of a pulse repetition frequency, a baseline position, a gain and a dynamic range is automatically set as a function of the plurality of signals after substantially discarding the identified signal.

In a second aspect, a system for automatic optimization in Doppler ultrasound imaging is provided. A Doppler processor is operable to detect a plurality of signals corresponding to a gate position in a patient. An optimization processor is operable to identify at least one signal from the plurality of signals, substantially discard the identified signal, and automatically set an imaging parameter or display characteristic as a function of the plurality of signals after substantially discarding the identified signal.

In a third aspect, maximum and minimum velocity traces are determined in a Doppler spectrum as a function of time. Portions of the maximum and minimum traces corresponding to a valve click are identified. A imaging parameter is automatically set as a function of the maximum and minimum traces without the identified portions.

In a fourth aspect, a method for automatic optimization and Doppler ultrasound imaging is provided. Spectral Doppler information is acquired in response to predetermined imaging parameters. One or more of the predetermined imaging parameters are automatically reset as a function of the spectral Doppler information acquired in response to the predetermined imaging parameters.

Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Automatic optimization for spectral Doppler imaging may provide better general, radiology or cardiology spectral imaging. Doppler data is acquired and analyzed to automatically set imaging parameters, such as the gain, dynamic range, scale or baseline associated with spectral Doppler imaging. Optimization is a function of data acquired using standardized or predetermined imaging parameters and/or signals where an artifact signal has been identified and discarded. For example, standardized or predetermined settings of the pulse repetition frequency, gain, dynamic range, and baseline are used to acquire Doppler data over about one heart cycle or over a time period. Other system settings (i.e. imaging parameters) may be predetermined, such as filter parameters, associated sensitivity for determining maximum or minimum velocity traces, or an amount of persistence for increasing signal-to-noise ratio. Based on the acquired Doppler data, the pulse repetition frequency or scale is set to just avoid aliasing, the dynamic range is set to match the signal dynamic range, a baseline is set to a proportional value, and a gain is set to minimize noise without losing signal. The performance of the optimization is independent of user settings. Any artifacts, such as associated with valve clicks, are identified and discarded for determining one or more of the optimum imaging parameter settings. Imaging parameter is used herein to include acquisition parameters (e.g., PRF), back-end parameters (e.g., gain and dynamic range) or other variable parameters that may alter the appearance of a continuous or pulse wave Doppler image.

Figure 1:
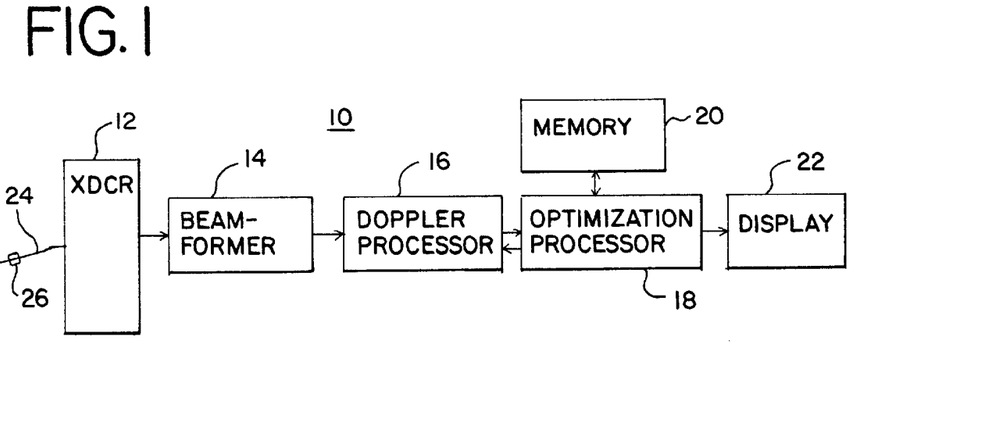
FIG. 1 is a block diagram of one embodiment of an ultrasound system for automatic optimization in Doppler ultrasound imaging.

FIG. 1 shows a block diagram of one embodiment of a system 10 for automatic optimization in Doppler ultrasound imaging. The system 10 includes a transducer 12, a beamformer 14, a Doppler processor 16, an optimization processor 18, a memory 20, and a display 22. Additional, different or fewer components may be provided, such as providing a separate gain stage, a scan converter or video mapping processors. The system 10 is any of now known or later developed ultrasound systems for generating spectral Doppler or other Doppler displays.

The transducer 12 is a ceramic or CMUT for transducing between acoustical and electrical energies. A single element, linear array of elements, or a multidimensional array of elements is provided for transmitting along a scan line 24 to a range gate position 26. The transducer 12 is also operable to receive information from the range gate 26 for generating a Doppler spectrum from multiple interrogations.

The beamformer 14 includes a transmit beamformation components, such as one or more waveform generators, memories or other devices for generating a unipolar, bipolar or complex waveform. The beamformer 14 also includes delays and amplifiers for applying relative delays and apodization to focus or transmit waveforms from a plurality of elements along the scan line 24 to the range gate 26. The transmissions for scanning along a scan line are repeated at a pulse repetition interval (i.e. 1/PRF where PRF is the pulse repetition frequency). The beamformer 14 is responsive to control signals to increase or decrease the pulse repetition frequency. Increasing the pulse repetition frequency may avoid aliasing, and decreasing the pulse repetition frequency may maximize the information obtained for the Doppler spectrum. An optimized pulse repetition frequency is close to the minimum value that avoids aliasing.

The beamformer 14 is a digital or analog beamformer for summing radio frequency signals generated by the elements of the transducer 12 in response to delays and apodization, identifying echo signals from the range gate position 26. Amplifiers, delays, delay lines, summers or other analog or digital devices generate beamformed ultrasound signals. Optionally, a demodulator generates in-phase and quadrature components representing the beamformed signal.

The Doppler processor 16 is an application specific integrated circuit, general processor, digital signal processor, analog circuit, digital circuit or other now known or later developed device for identifying velocity or frequency information and associated energy or power from the beamformed ultrasound signals. Optionally, a wall filter and corner turning memory may be provided. The Doppler processor 16 detects a plurality of signals corresponding to the gate position 26 of the patient for generating the spectral display. The Doppler processor 16 is operable to detect the Doppler spectrum from a plurality of interrogations of the gate 26. For example, the Doppler processor 16 applies a fast Fourier transform to identify a power or energy spectrum of velocities or frequencies at a given time. Many of various sliding windows, such as windows of 64 or 128 samples or interrogations of the range gate position 26 are included in each discrete Fourier transform. The Fourier transform generates frequency signals having values representing the magnitude of at least some of the Doppler component frequencies. In one embodiment, the Doppler processor 16 generates 8 bit log compressed power spectral data and 8 bit signed maximum and minimum waveforms, and transfers the information to the memory 20. Other resolutions or numbers of bits for the log compressed power spectrum or the minimum and maximum waveforms may be used.

In one embodiment, the Doppler processor 16 applies an overall gain to the generated Doppler spectrum. The Doppler processor 16 also applies a dynamic range by compressing the Doppler spectrum information within a desired range of values. The dynamic range window allows adjustment of the width of the window of input signal levels to be displayed. The gain control allows adjustment of the position of this window. For example, 256 discrete values are provided within the dynamic range and the dynamic range is selected to clip or saturate the energy or power values above and/or below the selected dynamic range. The gain may be applied before or after application of the dynamic range. Application of gain and dynamic range for pulse or continuous wave Doppler imaging is the same or similar to gain and dynamic range processes for B-mode imaging, such as disclosed in U.S. Pat. No. 6,398,733, the disclosure of which is incorporated herein by reference. Other independent processors or devices may be used for applying any of the gain or dynamic range, such as look-up tables.

The Doppler processor 16 determines the baseline position for the Doppler spectrum. The baseline represents the zero velocity point. The position of the baseline is determined as somewhere within the velocity scale. For example, where greater positive velocities are provided then negative velocities, the zero velocity level is set lower so that more of the display is associated with positive velocities then negative velocities.

The optimization processor 18 is an application specific integrated circuit, digital signal processor, general processor, control processor, digital circuit, analog circuit or other now known or later developed processor for optimizing Doppler imaging parameter settings. As shown, the optimization processor 18 is within the ultrasound data path, but an optimization processor 18 removed from the ultrasound data path may be provided. In alternative embodiments, the processing of the optimization processor 18 is dispersed among multiple processors or other devices distributed among other components of the system 10. For example, different functions of the optimization processor are performed by different processors. The optimization processor 18 controls the pulse repetition frequency, gain, dynamic range and baseline position, such as by providing control signals to the beamformer 14 and Doppler processor 16. The optimization processor 18 determines the parameter settings automatically as a function of Doppler ultrasound data, such as the Doppler spectrum signals. In one embodiment, the optimization processor 18 uses predetermined or standardized imaging parameters retrieved from the memory 20 for initially acquiring Doppler ultrasound data. The optimized parameters are then determined as a function of the initially acquired Doppler ultrasound data.

In an additional or alternative embodiment, the optimization processor 18 identifies an artifact signal, such as associated with a valve click, from a plurality of signals. For example, the optimization processor 18 determines a maximum and minimum velocity trace from the Doppler spectrum signals as a function of time or receives the traces from another processor or user input. Any Doppler spectrum and/or trace signals associated with artifacts are identified and discarded or minimized. As used herein, substantially discarded includes minimizing, such as through filtering or other processes, or replacing as well as removing. Any of various functions may be used to identify signals associated with artifacts, such as identifying discontinuities in the minimum or maximum velocity trace, identifying energy peaks by integrating the energy of the spectrum between the minimum and maximum velocity traces, identifying a change in the gradient along the time axis of the spectrum, identifying a high correlation with the first principal component of the spectrum representing highest variation, matching a template of an expected artifact with the spectrum or other methods. Once the artifact signals are substantially discarded, maximum and minimum trace signals over a time period are determined and anyone or more of the pulse repetition frequency and baseline position, gain and dynamic range are set as a function of the maximum and minimum trace signals. By discarding artifact signals in the Doppler spectrum signals, the gain and dynamic range are determined more optimally.

The memory 20 is a cache memory, RAM memory, corner turning memory, buffer or other memory device for storing maximum and minimum values, predetermined or standardized imaging parameters, minimum or maximum trace signals, Doppler spectrum signals, or other information utilized by the optimization processor 18.

The display 22 is a CRT monitor, flat panel display, LCD, plasma screen, touch screen, projector or other device for displaying the Doppler spectrum. The Doppler spectrum is a range of velocities displayed as a function of time. Various velocities at a given time are modulated as function of the power or energy of the velocity signal. The maximum and minimum traces associated with the envelope or velocities of the Doppler spectrum are overlaid on the spectrum image, but are not displayed in alternative embodiments. The maximum or highest possible positive value and minimum or lowest possible negative value define the range or velocity scale. The velocity and frequency are used interchangeably herein, where velocity, $V = cf_d/(2f_r \cos\theta)$ where c is equal to the speed of sound, $f_d$ is the Doppler shift frequency, $f_r$ is transmit frequency, and θ0 is the angle between the flow and the ultrasound beam. The angle may be assumed to be zero or may be accounted for in other embodiments. The Doppler shift frequency is less than or equal to half the pulse repetition frequency. Given the pulse repetition frequency, the maximum velocity that can be measured is determined. In one embodiment, the maximum pulse repetition or one over the maximum pulse repetition frequency is 25 kHz (i.e. PRI of 40 μs) for pulse wave Doppler transmissions. The displayed baseline is the zero velocity value within the velocity scale. The dynamic range and gain determine the intensity of the powers modulating the various velocities at any given time. Other imaging parameters may be used to affect other display features.

Figure 2:
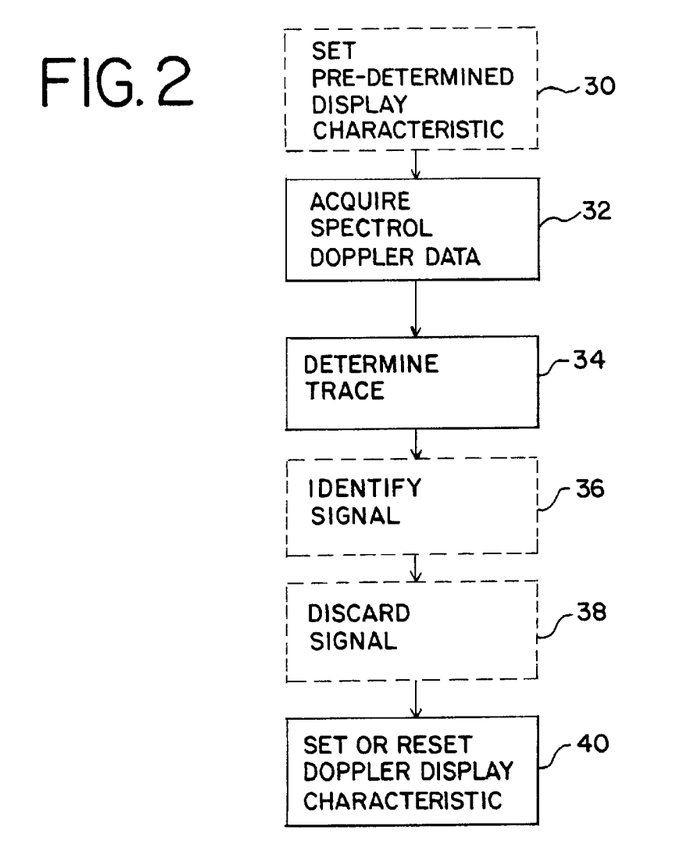
FIG. 2 is a flow chart diagram representing one embodiment of a method for automatic optimization in Doppler ultrasound imaging.

FIG. 2 shows a method for automatic optimization in Doppler ultrasound imaging of one embodiment. The method includes using both of a standardized or predetermined initial set of imaging parameters and discarding signals associated with artifacts for setting the optimized imaging parameters. In alternative embodiments, one or the other of the processes is used. For example, general Doppler spectral imaging is performed without identification and discarding signals associated with artifacts but with initial predetermined settings. As another example, cardiology spectral Doppler imaging is performed without using predetermined imaging parameters but with discarding of artifact signals. Additional, different or fewer acts than shown in FIG. 2 may be used.

Automatic optimization is performed by the system 10 without user input. Alternatively, the user selects (e.g., presses a button) or otherwise inputs instructions for the system 10 to perform automatic optimization.

In act 30, the spectral Doppler information is acquired in response to predetermined imaging parameters. Any of pulse repetition frequency, baseline position, gain or dynamic range and/or predetermined imaging parameter independent of direct and/or indirect user settings are used. In one embodiment, all of the above listed imaging parameters are predetermined, but one or more of the imaging parameters may be responsive to a user input. In yet other alternative embodiments, all of the above listed imaging parameters or other imaging parameters are configured in response to user settings rather than predetermination.

The predetermined pulse repetition frequency is set to be a greatest possible value given a particular transmit frequency. In alternative embodiments, lesser values of the pulse repetition frequency are used as the predetermined values. The greatest pulse repetition frequency value provides an increased scale to minimize a likelihood of aliasing. The pulse repetition frequency is directly related to the pulse repetition interval and scale. Using a predetermined value for the scale or pulse repetition interval is also using a predetermined value for the pulse repetition frequency. In cardiology imaging, the greatest PRF that avoids a high PRF mode may be used, assuring that range resolution is maintained.

The predetermined gain is a substantially zero or no gain. Zeroing the gain may limit the possibility of saturation or clipping of the spectral Doppler information. In alternative embodiments, a greater or lesser then zero gain is used as the predetermined value.

The predetermined dynamic range is the maximum possible dynamic range, such as 70 dB. The maximum dynamic range avoids or minimizes clipping or saturating spectral Doppler information. The dynamic range and gain are set so that for the widest variety of imaging situations, the highest possible signal-to-noise ratio is maintained over the entire image or spectrum. This ensures that areas where the signal is weak are taken into account by the optimization processor 18.

The predetermined baseline is set at a zero value corresponding to half way between the maximum and minimum velocities of the velocity scale. Other predetermined baseline values may be used, such as associated with including more positive or more negative information then negative or positive information, respectively.

Doppler spectral information is acquired in response to the predetermined imaging parameters in act 32. For example, Doppler spectral information over a single heart cycle, fraction of a heart cycle, multiple heart cycles, a time period, one second, or other time period is acquired. The acquired spectral Doppler signals are stored for or immediately used for determining optimized parameters.

In one embodiment, noise signals are acquired in addition to the plurality of spectral Doppler signals. The noise signals are acquired in response to the same predetermined imaging parameters. Unlike the spectral Doppler data, the noise data is received without transmission of acoustic energy. The noise spectrum is acquired over a lesser period than the Doppler spectral signal, such as acquiring over a 0.1 second or other fraction of a second, but a same or greater period may be used. The noise information and Doppler spectral signal information are used to determine the optimized gain and dynamic range. Optimized dynamic range is matched to the signal dynamic range above the mean noise, and optimized gain is set to map the mean noise level to 0.

In act 34, at least one of minimum or maximum velocity or frequency signals as a function of time is determined. For example, both maximum and minimum traces in the Doppler spectrum are determined as a function of time. Any of various algorithms or methods is used to determine the minimum and maximum velocity values of the Doppler spectrum signals. In one embodiment, any one or more of the techniques described in U.S. Pat. No. 5,868,676, the disclosure of which is incorporated herein by reference, are used. A noise threshold or average noise value is calculated or measured. For the maximum trace, the possible positive velocities are examined in order from highest to lowest. Where two consecutive velocities are provided above the noise or user set threshold, a maximum velocity is identified. Likewise, the minimum velocity 52 is identified as two consecutive values above the noise threshold when sequentially examining negative velocities starting with the extreme negative end of the scale. In alternative embodiments, other minimum and/or maximum trace algorithms may be used. In yet another alternative embodiment, the user identifies the maximum and minimum velocity traces 50, 52, by hand or the system 10 determines the traces in response to user input in part. Any now known or later developed techniques for determining either one of the minimum or maximum trace 50, 52 may be used.

Figure 3:
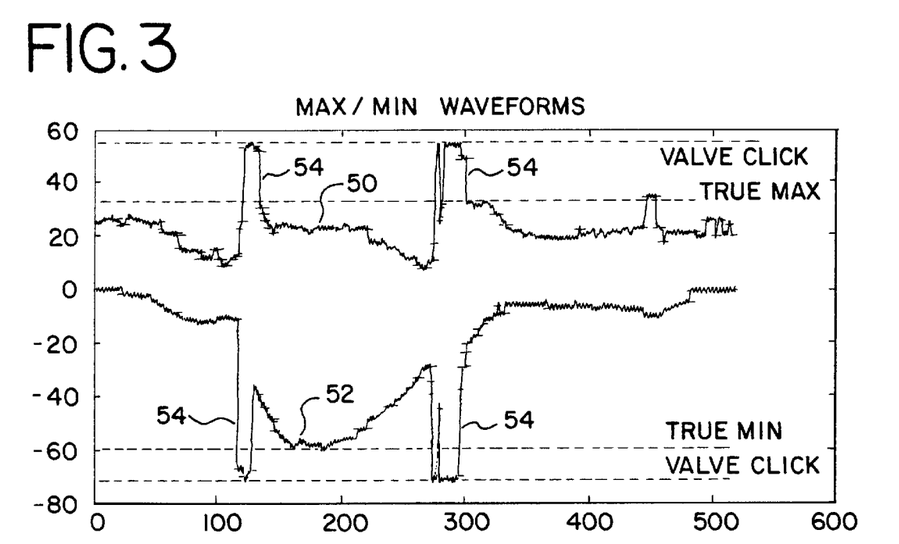
FIG. 3 is a graphical representation of one embodiment of maximum and minimum velocity traces of a spectrum envelope.

FIG. 3 shows a maximum velocity trace 50 and a minimum velocity trace 52 for an example Doppler spectrum where the X axis corresponds to time and the Y axis corresponds to velocity or frequency. Each of the minimum and maximum traces includes artifacts 54 from a valve click, such as associated with a range gate 26 positioned within a heart chamber.

For imaging applications where artifacts within the Doppler spectrum signals and/or minimum and maximum velocity trace signals are likely, the signals associated with the artifact are identified in act 36. In alternative embodiments, acts 36 and 38 are skipped, such as for applications in general Doppler spectral imaging where artifacts are unlikely or minimal. Signals associated with artifacts are directly identified or indirectly identified by determining signals associated with no artifact in act 36. For example, at least one signal or groups of signals corresponding to a valve click are identified from a plurality of signals, such as Doppler spectrum signals, maximum trace signals or minimum trace signals.

Any one or more of various methods may be used. Where a plurality of methods is used, all signals identified by each method, a logical selection of signals identified based on a comparison between the two methods or other algorithms may be used for selecting the signals. In one embodiment, the signal associated with an artifact is identified as a discontinuity in one of or both of the maximum and minimum traces where the discontinuity occurs as a function of time. For example, one or more of the methods for identifying valve click artifacts disclosed in U.S. Pat. No. 5,634,465, the disclosure of which is incorporated herein by reference, is used. This technique may also eliminate noise in the minimum and maximum velocity trace or Doppler spectrum. The maximum and minimum traces are assumed to be continuous over the acquisition time period and without aliasing.

Figure 4:
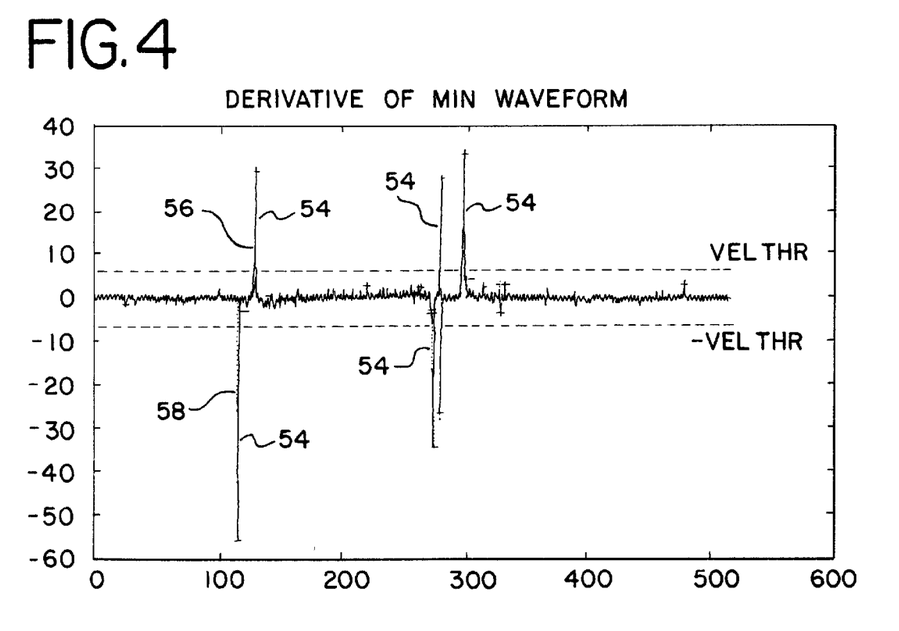
FIG. 4 is a graphical representation of a derivative of a minimum trace waveform in one embodiment for identifying an artifact.

In one example, first derivatives of the maximum and minimum velocity traces are examined to identify discontinuities. FIG. 4 shows the derivative 56 of the maximum trace. The valve clicks 54 are identified as the data between the spikes or acceleration along the derivatives 56, 58. In the positive velocity direction, a valve click is identified where the derivative is greater than a threshold followed by a derivative less than a negative threshold within a certain time period. Any of various thresholds may be used, such as constant or variable values. In one embodiment, the threshold is $0.1\ V_{NYQ}$ where $V_{NYQ}$ is the Nyquist velocity. Other acceleration thresholds may be used. The certain time period or amount of time between the positive and negative derivatives is a constant or variable value and may be selected based on an expected or experimentally determined duration of valve clicks or other artifacts. For example, where the minimum and maximum velocity trace is low pass filtered or otherwise averaged, the signals from valve clicks may have a longer duration. Where a patient may have prosthetic valves, the duration may be longer than for patients with native valves. In one embodiment, the duration is selected as 40 ms, but other values may be used. The duration parameter is used to distinguish valve click artifacts from other phenomena, such as for an aortic regurgitation. For aortic regurgitation, the velocities and associate minimum and maximum traces may rise rapidly, but the duration is substantially longer than for valve clicks or other artifacts.

Figure 5:
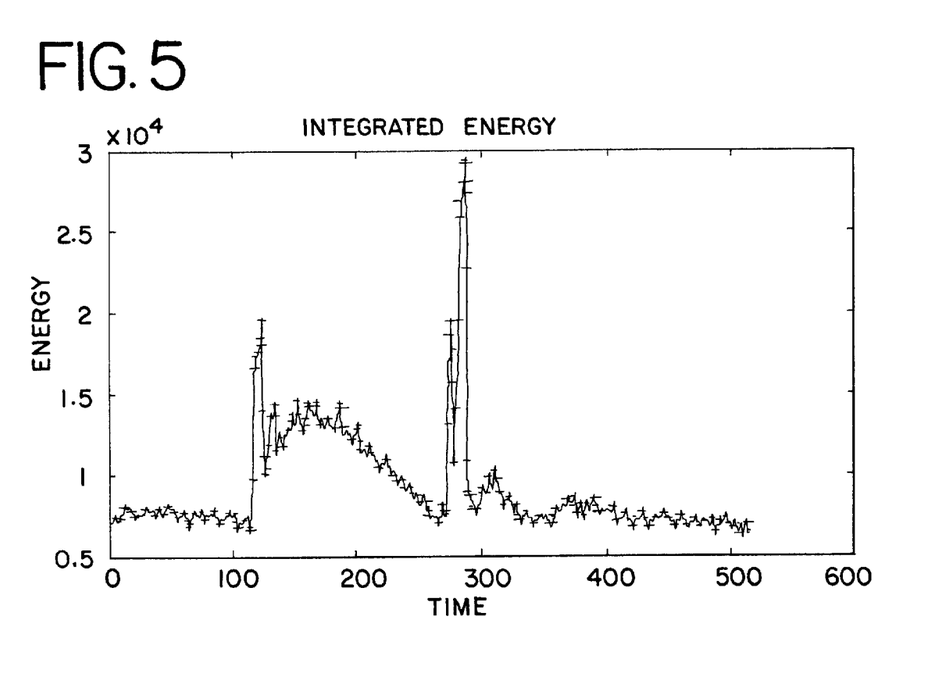
FIG. 5 is a graphical representation of one embodiment of integrated energy used to identify an artifact.

In an alternative embodiment, artifact signals are identified as a function of the integrated energy of the Doppler spectrum or of the velocity signals between the maximum and minimum velocity traces as a function of time. For example, the power or energy for all of the velocities in the Doppler spectrum for each time sample is integrated. FIG. 5 shows the integration of the energies associated with the Doppler spectrum used for FIG. 3. Since the energies are always positive, the summation within each time results in a positive value. Signals corresponding to times where the energy exceeds a threshold are identified as artifacts. The threshold may be constant or variable, such as threshold based on a median or average energy in a moving window or for all samples. Alternatively, signals corresponding to times of the top two integrated energy peaks within a heart cycle or a particular time period may be identified as artifacts. A neighborhood of values, such as associated with a plurality of times centered around the energy peaks are identified as being artifact signals. The size of the window may depend on experimental results or application. For example, a greater window size for identifying a range of times associated with an artifact is greater where the maximum and minimum waveforms are low pass filtered.

In another embodiment, a signal associated with an artifact is identified based on a change in the gradient in the Doppler spectrum. Vertical edges in the Doppler spectrum or energy values indicate valve clicks or other artifacts. Vertical edges correspond to rapid or sudden increases in velocity along the time scale. The edges are detected in any of various techniques, such as treating the Doppler spectrum as a gray scale image. Vertical edges are identified by thresholding a gradient along the X or time dimension or by using a directional edge detector such as SOBEL, PREWITT, or ROBERTS discrete approximations to the gradient. To reduce sensitivity to noise, a low pass or other filter, such as an infinite impulse response filter is applied along the X or time dimension.

In another method, a signal or signals associated with artifacts are identified as a function of deviation from an expected pattern, such as a deviation in the expected pattern of Doppler spectrum and/or the minimum and maximum velocity trace signals as a function of time. Any of modeling or correlation techniques may be used. In one embodiment, an average spectrum based on statistics or other experimentation for a particular application or in general or a desired spectrum is modeled. The acquired spectral information is checked against the average or desired spectrum. Where the receive data matches the model for an artifact portion, the artifact signals are identified. Alternatively, deviations from the desired data are identified as artifacts. For example, a principle component analysis of the spectrum is used to detect valve clicks. An orthogonal set of basis vectors describing a data set using fewer dimensions then the original spectral data set are determined. The velocities are treated as a vector of a random variable and each time sample as one observation of the random vector. The eigenvector of the covariant matrix corresponding to the largest eigenvalue is defined to be the first principle component. Let $v(t)=[v1(t)\ v2(t)\ \ldots\ vN(t)]$ be the random vector of velocities at a given time t. T observations of this random vector: $t=1,\ldots T$ are assumed to exist. Form the covariance matrix K(v) (size N×N):

$$K(n,m)=\Sigma_t v_n(t)\ v_m(t)-(\Sigma_t v_n(t))\ (\Sigma_t v_m(t))$$

The eigenvectors and eigenvalues of K are found such that:

$$K*E=E*D$$

where the columns of E are the eigenvectors of K and D is a diagonal matrix of eigenvalues corresponding to the eigenvectors in E. The column of E that corresponds to the largest eigenvalue in D is the first principal component. This vector E1 accounts for $(D1*100/\Sigma D)$ % of the total variation in the dataset and a peak in the correlation between this eigenvector and the spectrum at a given time can be used to identify valve clicks.

Figure 6:
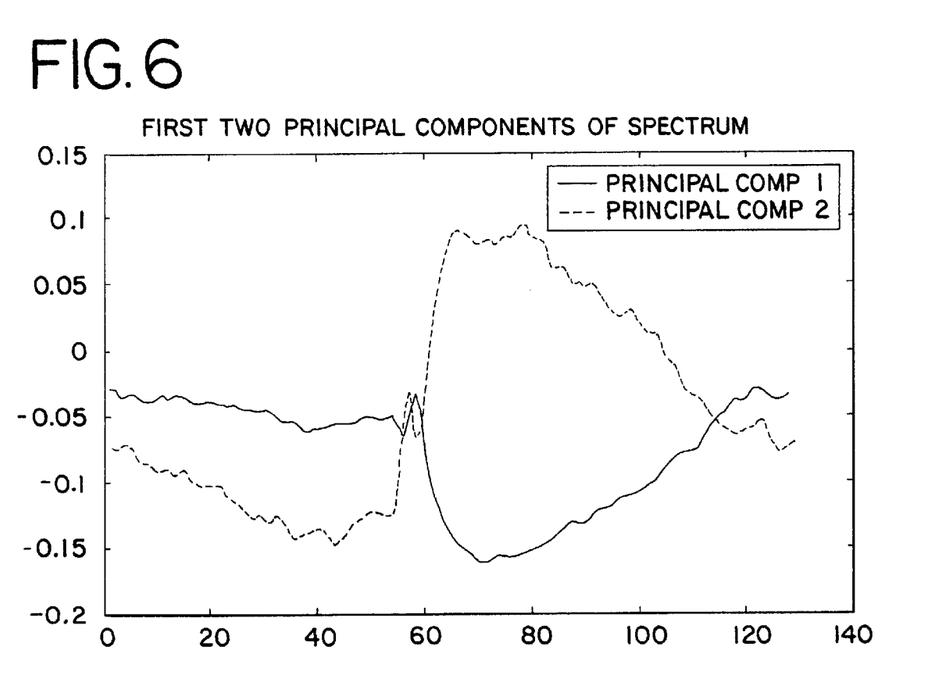
FIGS. 6 and 7 are graphical representations of one embodiment for identifying an artifact using a model waveform.
Figure 7:
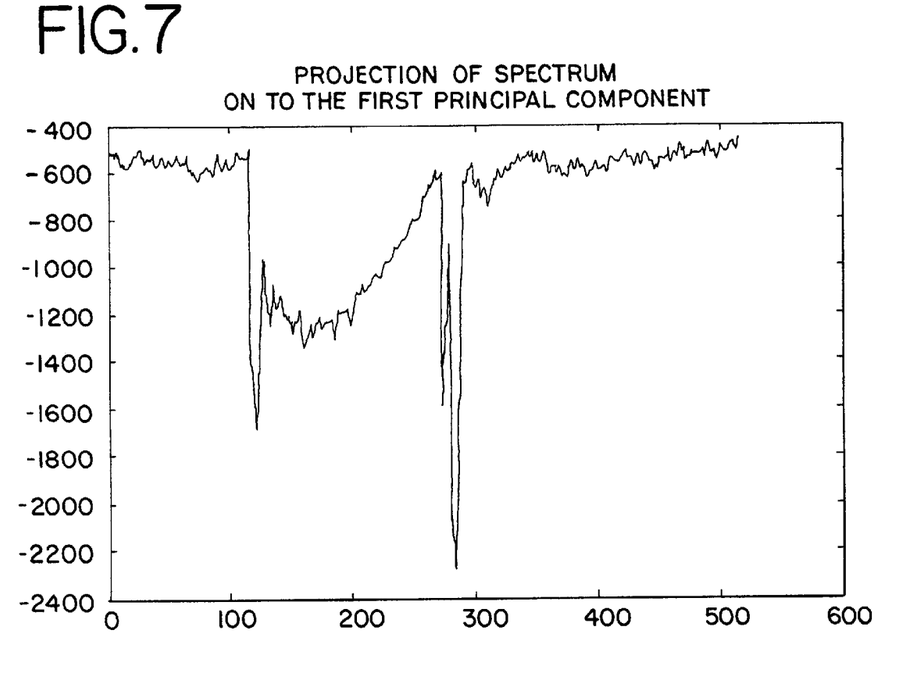

Data projected onto the first principle component has the highest variance. Peaks in the correlation between the first principle component and a particular observation of the random vector indicates that the observation causes the maximum variation within the data set. Valve clicks are identified as the peaks of the projection of the data set onto the first principle component. In one embodiment, the principle components of an average, experimental or desired spectrum are generated and stored prior to acquisition of the Doppler spectral data for imaging. The artifacts are then identified in real time by thresholding the projection onto the first principle component. Alternatively, non-real time or subsequent analysis is used. FIG. 6 shows two principle components of an average or modeled spectrum. The first principle component accounts for approximately 59% of the total variation and the second component accounts for approximately 14% of the total variation of the data set. FIG. 7 shows the Doppler spectrum of the acquired data projected onto the first principle component of the acquired Doppler spectrum. The valve clicks or other artifacts correspond to the peaks in the projection. While the sign of the correlation is shown as negative, the principle components form a orthogonal set so the vectors can be reversed in direction, resulting in a positive sign. Other techniques for modeling may be used.

Figure 8:
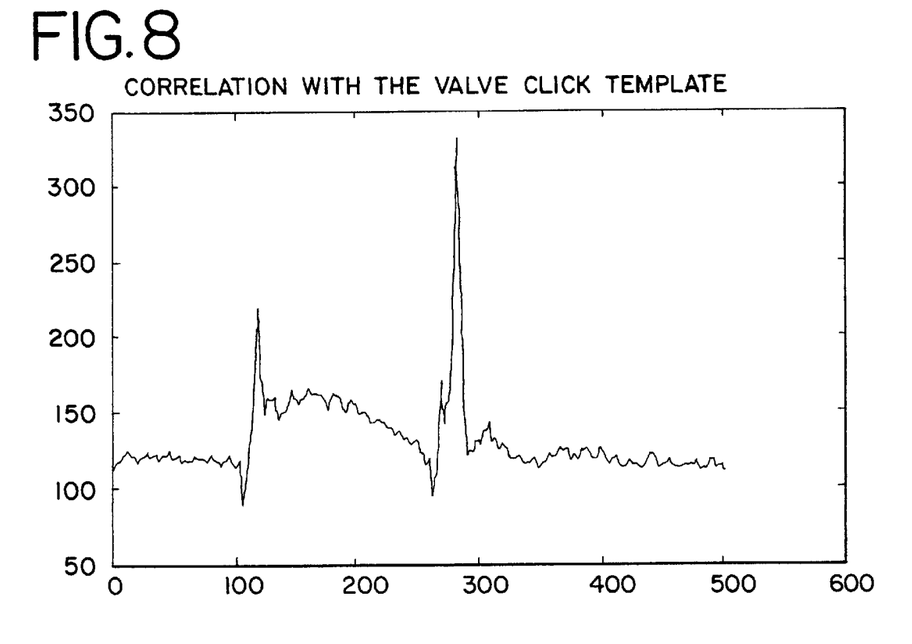
FIG. 8 is a graphical representation of one embodiment of identifying a signal artifact using a correlation with an expected artifact.

In yet another technique, an artifact signal is identified as a function of a template match with at least one of the maximum and minimum signals or with the Doppler spectrum data. The template representing an expected artifact, such as a valve click of 40 ms or a certain number of time samples, is correlated with the minimum and maximum traces or the Doppler spectrum. For example, the template includes decreasing energy characteristics from the baseline for a comparison with energy characteristics of the Doppler spectrum. Since the valve click artifacts energy is strongest at the baseline, energy characteristics may better define a artifact. Alternatively, velocity values or minimum and maximum trace valves are correlated with the template. The template is repetitively positioned at different temporal positions relative to the Doppler spectrum or traces for calculating correlation coefficient as a function of time. The correlation coefficient between the Doppler spectrum or minimum and maximum traces and the template is computed. Other correlations may be calculated. FIG. 8 shows peaks in the correlation function corresponding to the valve click artifacts.

Other methods for identifying an artifact from the Doppler spectral data or the minimum and maximum traces may be used. Any of the above-described methods or other methods may identify deviations from artifact free information or identify artifacts based on a similarity to an expected artifact.

In act 38, the signal or signals corresponding to an identified artifact are substantially discarded from the remaining signals. The signal to be discarded is one or multiple of maximum trace signals, minimum trace signals, or Doppler spectrum signals. Substantially is used herein to account for discarding some signals associated with no artifact or discarding only a portion of the signals associated with an artifact. The beginning and end time period associated with an artifact are identified. The data between the beginning and end time periods is discarded. The artifact data is either removed from the signals, such as removing all Doppler spectra or minimum and maximum trace information associated with particular time periods. Alternatively, the signals are discarded by processing that ignores the identified signals. Alternatively, the identified artifact signals are discarded by altering or replacing the artifact signals with signals corresponding to an expected signal free of an artifact. In yet other alternative embodiments, data is not discarded, such as where the acquired spectral data is free of artifacts or where identification of artifacts is turned off or not used.

In act 40, one or more of the imaging parameters is automatically set or reset. For example, all of the pulse repetition frequency, the baseline position, the gain and the dynamic range are reset as a function of the spectral Doppler information acquired in act 32. For example, an imaging parameter is adjusted from the predetermined imaging parameter without user adjustment. As another example, an imaging parameter is automatically set as a function of the maximum and minimum traces without the portions identified as corresponding to artifacts. As yet another example, an imaging parameter is automatically set as a function of the plurality of signals, such as Doppler spectral signals, after substantially discarding signals identified as associated with artifacts. In one embodiment, a subset or all of the pulse repetition frequency (e.g. velocity scale), a base line position, a gain (e.g., back-end gain (detected data gain) as opposed to front-end or beamformer gain), and a dynamic range are automatically set by the optimization processor 18 as a function of a plurality of ultrasound signals, but other imaging parameters may alternatively or additionally be set automatically. In embodiments where the gain and dynamic range are automatically optimized, determination of the minimum and maximum velocity traces are or are not performed.

In one embodiment, an imaging parameter is set as a function of maximum and minimum signals selected from the plurality of signals (e.g. trace) over a time period. For example, one maximum and one minimum velocity are selected from maximum and minimum traces free of signal artifacts over a one second or one heart beat time period. By discarding signals associated with artifacts, the maximum and minimum velocities within the time period are free of even greater maximum or even lesser minimum signals caused by artifacts. For example, over a 500 millisecond time period shown in FIG. 3 (e.g., 512 samples at 2 ms intervals corresponding to 1 sec), a maximum velocity of 33 occurring at about 310 microseconds is selected as the maximum velocity and a minimum velocity of minus 55 occurring at about 190 microseconds is selected as the minimum velocity. The maximum velocity of 55 and the minimum velocity of −70 associated with the artifacts are not selected.

In one embodiment, the pulse repetition frequency is set or reset as a function of the maximum and minimum velocities. For example, a user set pulse repetition frequency or a predetermined pulse repetition frequency is weighted by (maximum velocity minus minimum velocity)/128. In alternative embodiments, a pulse repetition frequency is calculated directly from the maximum value, the minimum value, and/or other signals. In the calculation discussed above, 128 different velocities are provided within the imaging (Nyquist) range, but other numbers of velocities may be measured without aliasing. The reduction in the pulse repetition frequency maximizes the information content without aliasing. To further avoid aliasing, the calculated pulse repetition frequency may be increased, such as increasing by one discrete setting provided by the system or increasing by a factor, such as a weighting factor or an added factor. In one embodiment, the pulse repetition frequency continues to be automatically set based on previous heart cycles such as averaging the minimum or maximum over multiple heart cycles or selecting a maximum and minimum over several heart cycles. Alternatively, the pulse repetition frequency is reset periodically or only once determined as described herein.

In one further embodiment, an algorithm automatically detects an cardiac arrhythmia, resulting in little or no signal during the 1 sec of data acquisition. In the case of an arrhythmia, the Doppler spectral information is acquired over multiple heart cycles to properly identify the maximum and minimum values.

The base line imaging parameter is also determined as a function of the identified maximum and minimum velocities in one embodiment. The base line is determined as a normalized value between −1 and 1. The base line is equal to.

$$2\left|\frac{\min.\ vel.}{\max vel.\ -\ \min vel.}\right| - 1.$$

Other equations or techniques for calculating the base line from any of various signal information may be used. The baseline is then set within the 128 or other number of velocity units along the Y axis where a baseline of −1 corresponds to −64 in velocity units and +1 corresponds to +63. For example, the baseline of +0.09 shown in FIG. 3 is set so that a greater range of negative velocity values (−70) are provided than positive velocity values (+57).

One or more of the imaging parameters are set or reset as a function of noise data and Doppler spectral signals. The signals are acquired in act 32 based on user set or predetermined imaging parameters. In one embodiment, the signal data is substantially free of data associated with artifacts, such as by identifying and substantially discarding such signal data.

The gain and dynamic range are automatically set or reset as a function of both noise data and Doppler spectral signals. A lower and an upper signal threshold are identified for setting the dynamic range, and the signals between these thresholds are mapped to display gray scale levels. In one embodiment, the system 10 includes 256 discrete levels for mapping the amplitude of the Doppler spectrum to grayscale display levels, but other numbers of levels may be used. A mean noise is computed from the noise signals acquired with the transmitters turned off. The lower signal threshold is set as a function of the mean noise value, such as being at the mean noise value or set at a level above or below the mean noise value. A user-controlled target spectral intensity parameter may determine the offset to mean noise to define the lower threshold. The upper threshold is determined from the maximum signal level or from the highest signal level associated with a particular distribution of signals. Any of various thresholds based on distributions of the signals may be used. The dynamic range is then set as a function of the previous dynamic range used to acquire the Doppler spectral signals. For example, the new dynamic range is equal to the previous predetermined or user set dynamic range weighted by $$\frac{U_T - L_T}{255}$$

(where $U_T$ is the upper threshold, $L_T$ is the lower threshold, and 255 is the number of mapping levels, such as 255 where a 0 value is set as the noise or no signal floor. The dynamic range of the display is matched to the dynamic range of the signal in this embodiment.

In one embodiment, the gain is determined as a function of the dynamic range. Like the dynamic range, the gain is a function of Doppler spectral signals acquired in act 38 as well as the noise information. In one embodiment, the gain is determined to center a dynamic range window between the lower and upper signal thresholds. This assures that the mean noise with or without a user or system defined offset is mapped to 0 gray scale value whereas the maximum signal level is mapped to a 255 value. A new gain is set as a function of the gain used to previously acquire data. For example, if the system 10 keeps the gray level of mapped to the midpoint of the current dynamic range ('pivot') constant while changing the dynamic range, a dynamic range center offset is defined to be equal to half the number of levels (e.g. 127.5) minus an average of the upper and lower thresholds. The new gain is then equal to the previous gain plus the dynamic range center offset times the previous dynamic range divided by 255, the number of signal levels used for display. Other functions for determining the gain may be used depending on how the system 'pivots' the dynamic range window.

In one embodiment, the change in the dynamic range from a predetermined or a user set of value is restricted. For example, the dynamic range is restricted to vary within plus or minus 10 dB around a target dynamic range. In low signal to noise ratio situations, the restricted dynamic range forces a minimum dynamic range for optimization. This means the signal's dynamic range is less than the system dynamic range and not all of the 256 display gray levels are used. Users typically increase gain in low SNR situations, and decreasing the lower threshold for a fixed dynamic range has the effect of increasing gain for the gain calculation described above. Therefore, the lower threshold may be decreased adaptively as a function of SNR (as measured by the difference between the minimum allowed dynamic range (target −10dB)) and the signal's dynamic range as measured by $$\frac{U_T - L_T}{255} DNR_{old}.$$

The upper threshold is then re-calculated from $$\min\_DNR = \frac{U_T - U_T}{255} DNR_{old}$$

and gain is calculated as described above. In another method, the lower signal threshold is fixed and the upper signal threshold is calculated based on the fixed lower signal threshold without adaptively increasing gain for low SNR situations.

The gain and dynamic range calculated as discussed above are based on zero setting of the user-input target spectral intensity parameter. In high signal-to-noise ratio applications, such as a carotid examination, the user may desire greater noise rejection. Target spectral intensity may be set to a negative value, increasing the lower signal threshold to more likely clip noise signals. Such change in a lower signal threshold is determined automatically as a function of a selected application or in response to user input.

While the invention has been described above by reference to various embodiments, it should be understood that many changes and modifications can be made without departing from the scope of the invention. For example, the discussion above is generally directed to pulsed wave Doppler imaging. The processes and systems may also be used with continuous wave Doppler imaging. For continuous wave Doppler imaging, the signal repetition interval is set or adjusted instead of the pulse repetition interval and no upper (Nyquist) limit for velocities is measured. Velocity and frequency are directly related, so the terms frequency and velocity are used interchangeably.

It is therefore intended that the foregoing detailed description be regarded as illustrative rather than limiting, and that it be understood that it is the following claims, including all equivalents, that are intended to define the spirit and scope of this invention.

What is claimed is:

1. A method for automatic optimization in Doppler ultrasound imaging, the method comprising:
    (a) identifying at least a first signal in a plurality of signals from a gate position in a patient;
    (b) substantially discarding the at least first signal from the plurality of signals; and
    (c) automatically setting at least one of: a pulse repetition frequency, a baseline position, a gain and a dynamic range as a function of the plurality of signals after substantially discarding the at least first signal.

2. The method of claim 1 wherein (c) comprises setting the pulse repetition frequency.

3. The method of claim 1 wherein (c) comprises setting the baseline position.

4. The method of claim 1 wherein (c) comprises setting the back-end gain.

5. The method of claim 1 wherein (c) comprises setting the dynamic range.

6. The method of claim 1 wherein (c) comprises setting as a function of a maximum and minimum velocity signal of the plurality of signals over a time period.

7. The method of claim 1 further comprising:
    (d) determining at least one of a maximum and minimum velocity of the plurality of signals as a function of time;
    wherein (a) comprises identifying the first signal as a function of a discontinuity in the at least one of the maximum and minimum velocity as a function of time.

8. The method of claim 1 further comprising:
    (d) determining at least one of a maximum and minimum velocity of the plurality of signals as a function of time;
    wherein (a) comprises identifying the first signal as a function of integrated energy for velocity signals between the maximum and minimum as a function of time.

9. The method of claim 1 further comprising:
    (d) determining at least one of a maximum and minimum velocity of the plurality of signals as a function of time;
    wherein (a) comprises identifying the first signal as a function of a change in gradient in the Doppler spectrum as a function of time.

10. The method of claim 1 further comprising:
    (d) determining at least one of a maximum and minimum velocity of the plurality of signals as a function of time;
    wherein (a) comprises identifying the first signal as a function of a deviation from an expected pattern.

11. The method of claim 1 further comprising:
    (d) determining at least one of a maximum and minimum velocity of the plurality of signals as a function of time;
    wherein (a) comprises identifying the first signal as a function of a template match.

12. The method of claim 1 wherein (a) comprises identifying the first signal as corresponding to a valve click, (b) comprises discarding the first signal and (c) comprises setting as a function of at least one of: a minimum velocity, a maximum velocity and the amplitude of the Doppler spectrum.

13. A system for automatic optimization in Doppler ultrasound imaging, the system comprising:
    a Doppler processor for detecting a plurality of signals corresponding to a gate position in a patient; and
    an optimization processor for identifying at least a first signal from the plurality of signals, substantially discarding the at least first signal from the plurality of signals, and automatically setting at least one of: a pulse repetition frequency, a baseline position, a gain and a dynamic range as a function of the plurality of signals after substantially discarding the at least first signal.

14. The system of claim 13 wherein the optimization processor is operable to setting the pulse repetition frequency.

15. The system of claim 13 wherein the optimization processor is operable to set one of the pulse repetition frequency and baseline position as a function of a maximum and minimum signal of the plurality of signals over a time period.

16. The system of claim 13 wherein the optimization processor is operable to determine at least one of a maximum and minimum velocity trace of the plurality of signals as a function of time and identify the first signal as a function of at least one of: a discontinuity in the at least one of the maximum and minimum trace, integrated energy for velocity signals between the maximum and minimum trace, a change in gradient in the Doppler spectrum, a deviation from an expected pattern in the Doppler spectrum, and a template match with the at least one of the maximum trace, the minimum trace and the Doppler spectrum.

17. A method for automatic optimization in cardiology Doppler ultrasound imaging, the method comprising:

(a) determining maximum and minimum velocity traces in a Doppler spectrum as a function of time;

(b) identifying portions of the maximum and minimum traces corresponding to a valve click; and (c) automatically setting an imaging parameter as a function of the maximum and minimum traces without the identified portions.

18. The method of claim 17 wherein (c) comprises automatically setting the imaging parameter as at least one of: a pulse repetition frequency and a baseline position.

19. The method of claim 17 wherein (b) comprises identifying the portions as a function of at least one of: discontinuities in the maximum and minimum traces, integrated energy for velocity signals between the maximum and minimum traces, a change in gradient of Doppler spectrum, a deviation from an expected pattern in the Doppler spectrum, and a template match with one of the maximum trace, the minimum trace and the Doppler spectrum.

20. The method of claim 17 wherein (c) comprises automatically setting a velocity scale.

21. A method for automatic optimization in Doppler ultrasound imaging, the method comprising:

(a) acquiring spectral Doppler information in response to a pre-determined value of an imaging parameter from the group of: a pulse repetition frequency, a baseline position, a gain and a dynamic range, the pre-determined value independent of a user setting of the imaging parameter; and (b) automatically re-setting at least one of: the pulse repetition frequency, the baseline position, the gain and the dynamic range as a function of the spectral Doppler information acquired in (a).

22. The method of claim 21 wherein (a) comprises acquiring the spectral Doppler information in response to a pre-determined pulse repetition frequency comprising a substantially greatest pulse repetition frequency given a transmit frequency.

23. The method of claim 21 wherein (a) comprises acquiring the spectral Doppler information in response to a pre-determined gain.

24. The method of claim 21 wherein (a) comprises acquiring the spectral Doppler information in response to a pre-determined dynamic range comprising a substantially maximum dynamic range.

25. The method of claim 21 wherein (b) comprises adjusting the imaging parameter from the pre-determined value without user adjustment of the imaging parameter.

26. The method of claim 21 wherein (a) comprises acquiring the spectral Doppler information in response to a plurality of pre-determined values comprising the pulse repetition frequency, the baseline position, the gain and the dynamic range, and (b) comprises automatically re-setting each of the pulse repetition frequency, the baseline position, the gain and the dynamic range as a function of the spectral Doppler information acquired in (a).

27. The method of claim 21 wherein (a) comprises acquiring noise data and signal data and (b) comprises automatically resetting as a function of both the noise data and the signal data.

28. The method of claim 21 further comprising:

(c) determining at least one of maximum and minimum velocity traces in the spectral Doppler information as a function of time;

(d) identifying at least a first signal in the at least one of maximum and minimum velocity traces; and (b) substantially discarding the at least first signal from the at least one of maximum and minimum velocity traces;

wherein (b) comprises automatically re-setting as a function of the at least one of maximum and minimum traces after substantially discarding the at least first signal.

* * * * *